United States Patent [19]

Sherman

[11] Patent Number: 5,036,838
[45] Date of Patent: Aug. 6, 1991

[54] FOAM PLASTIC ORTHOPEDIC FABRIC

[75] Inventor: Harry A. Sherman, Flushing, N.Y.

[73] Assignee: Applied Technology International, Ltd., West Chester, Pa.

[21] Appl. No.: 552,830

[22] Filed: Jul. 16, 1990

[51] Int. Cl.⁵ ............... A61F 13/00; A61L 15/00
[52] U.S. Cl. .................... 128/155; 128/156; 128/DIG. 15
[58] Field of Search ............... 128/77, 89 R, 878, 879, 128/87 R, 155, 156, 876, 165, 96.1, DIG. 15

[56] References Cited

U.S. PATENT DOCUMENTS

| 3,086,529 | 4/1963 | Munz | 128/96.1 |
|---|---|---|---|
| 3,256,882 | 6/1966 | Huber | 128/165 |
| 3,458,867 | 8/1969 | Moore | 128/165 |
| 4,027,666 | 6/1977 | Marx | 128/165 |
| 4,048,991 | 9/1977 | Marx | 128/77 |
| 4,401,113 | 8/1983 | Incorvaia | 128/165 |
| 4,441,490 | 4/1984 | Nirschl | 128/77 |
| 4,441,493 | 4/1984 | Nirschl | 128/165 |
| 4,476,857 | 10/1984 | Levine | 128/77 |
| 4,832,010 | 5/1989 | Lerman | 128/77 |
| 4,854,309 | 8/1989 | Elsey | 128/165 |
| 4,921,743 | 5/1990 | Hansen | 128/165 |

Primary Examiner—Robert A. Hafer
Assistant Examiner—Michael Brown
Attorney, Agent, or Firm—Eckert Seamans Cherin & Mellott

[57] ABSTRACT

An orthopedic fabric is disclosed which includes a length of unbroken loop fabric to which is intimately adhered a layer of thermoplastic breathable elastomeric foam without employing stitches or other additional materials. The unbroken loop fabric may be stretchable for use as a support device or non-stretchable for use as an immobilizing device. The thermoplastic foam layer may be cured directly upon the unbroken loop fabric or may be intimately bonded by employing ultrasonic frequency, radio frequency or thermal energy sufficient to melt surface portions of the foam layer causing it to become adhesive.

19 Claims, 1 Drawing Sheet

FOAM PLASTIC ORTHOPEDIC FABRIC

BACKGROUND OF THE INVENTION

1. Field of the Invention

The present invention relates generally to the field of elasticized orthopedic devices suitable to be applied on or about portions of the body, and more particularly, is directed to a reusable, bonded, urethane based, thermoplastic foam layer that is intimately adhered to an elasticized fabric substrate having fastening properties.

2. Discussion of the Prior Art

Quite often, for example due to trauma or illness, portions of the human body require additional exterior support in order to perform such usual functions as walking, running, throwing and the like. In order to be compatible for use directly upon portions of the human anatomy, such supports have traditionally taken the form of some type of elasticized fabric which can be applied directly about or wrapped around the portion of the user's body that is required to be reinforced and supported, for example, ankles, knees, wrists, elbows and the like. Elasticized tubular materials having suitable size and shape for use about the knees, and wrists, etc. of a wearer can be purchased at all well-equipped drug stores and similar establishments and such devices have been and are being are produced by many various manufacturers, both in the United States and in foreign countries.

Additionally, elongated lengths of elasticized fabric known popularly as "Ace" bandages can also be readily found in drug stores and similar establishments for use to wrap around and to support various portions of the human body when necessary. The "Ace" type bandages find a particular utility in binding and otherwise supporting irregularly shaped portions of the human anatomy, for example, arches, ankles knees, back, elbows and the like. Such type of bandages can be readily applied simply by wrapping the body portions to be supported with repeated turns of the bandage until the entire area to be treated is adequately covered. The free end of the "Ace" type bandages can then be secured in position by butterfly clips or other fastening devices suitable for the use to prevent unwanted unraveling.

In U.S. Pat. Nos. 4,392,487 and 4,753,228, there is disclosed an apparatus for foot stabilization which consists essentially of an elasticized sleeve which is designed to overfit the foot of the wearer and an attached, elongated strap of limited elasticity which is intended to be wrapped around the foot in a particular manner. The sleeve is fabricated about a portion of its exterior surface with a fabric having fastening properties such as "VELCRO" brand material for interconnecting with cooperating hook portion fastening material provided at the free end of the strap. One such apparatus for foot stabilization is presently being manufactured and sold by Resupinator Company of Studio City, Calif. 91609. The Resupinator Company construction includes a plurality of stitched seams to join the various fabrics and portions together and is fabricated to a specific size and shape for the intended use. Accordingly, this apparatus for foot stabilization has limited utility and is relatively expensive in manufacture in view of the number of hand operations involved in the manufacture.

SUMMARY OF THE INVENTION

The present invention relates generally to the field of flexible orthopedic devices suitable for support application about portions of the body, and more particularly, is directed to an orthopedic device of universal application comprising a thermoplastic polyurethane foam layer bonded to an elasticized fabric substrate.

The foam plastic orthopedic fabric of the present invention comprises a thermoplastic foam layer that has been intimately adhered to an elasticized substrate fabric of suitable, required length. The substrate should preferably be fabricated of a known unbroken loop fabric having fastening properties, similar to that of "VELCRO" brand material, which can be quickly fastened to and released from a cooperating hook-type fastening material. At one end of each length of foam plastic orthopedic fabric is secured a suitable short length of "VELCRO" brand or other similar hook type material having fastening properties of known construction. The short length of material having fastening properties can be securely affixed to the end of the orthopedic fabric by non-stitched means, such as by ultrasonic welding, radio frequency sealing or heat sealing in known manner.

The thermoplastic foam which preferably is urethane based may be foamed directly upon the "VELCRO" brand or other similar unbroken loop fabric having fastening properties substrate or may be adhesively bonded thereon in known manner by using available thermoplastic foam adhering techniques. Alternately, the foam layer may be adhered to the elasticized or non-elasticized fabric substrate by a known type of transfer coating process, that is, by first casting the foam layer upon a sheet of release paper and then, prior to complete curing, removing the transfer sheet and applying the thermoplastic foam layer directly upon the elasticized fabric layer and then permanently bonding the layers together utilizing suitable pressure.

It is also contemplated that the thermoplastic foam layer and the elasticized or non-elasticized fabric substrate can be intimately secured together in overall bonding by employing a flame laminating process. That is, in known manner, a previously formed thermoplastic foam layer can be exposed to a flame under controlled conditions to partially liquify the foam layer surface. Upon application of an elasticized or non-elasticized fabric substrate to the heat liquified foam layer surface, the two layers can be intimately and permanently bonded together completely throughout the respective contacting surfaces.

The thermoplastic foam layer of the present invention provides a non-toxic, breathable, cushioning support device which is intended to be applied directly to portions of the body and which can even be used directly upon an open wound. Heat sealing, ultrasonic welding or other similar plastic forming techniques are employed throughout in a manner to permit fabrication of the orthopedic fabric by utilizing automatic equipment and without requiring any hand stitching or other manual operations in order to form the finished fabric.

Additionally, it is contemplated that the selective application of electrostatically deposited flock directly into the foam layer without the use of adhesives could be applied during the curing of the foam. The flock will create a soft surface in known manner to thereby enhance breathability of the foam and increase moisture-vapor transfer (disapation), all in a manner to prevent chafing.

It is therefore an object of the present invention to provide an improved foam plastic orthopedic fabric of the type set forth.

It is another object of the present invention to provide a novel foam plastic orthopedic fabric having all components heat sealed or otherwise secured together without requiring manual operations.

It is another object of the present invention to provide a foam plastic orthopedic fabric comprising in combination a stretchable "VELCRO" brand or similar fastening material layer bonded to a stretchable thermoplastic foam layer and a "VELCRO" brand or similar hook fastener strip that is heat sealed or otherwise adhered to one of the bonded layers without employing stitching.

It is another object of the present invention to provide a novel foam plastic orthopedic fabric comprising bonded first and second stretchable layers secured together without sewing or stitches in combination with a hook type fastener that is heat sealed to one or both of the layers and which is capable of removably securing to one of the bonded layers for securing the orthopedic fabric about a portion of the body to be treated.

It is another object of the present invention to provide a novel foam plastic orthopedic fabric that is simple in design, inexpensive in manufacture and highly efficient when in use.

Other objects and a fuller understanding of the invention will be had by referring to the following description and claims of a preferred embodiment thereof, taken in conjunction with the accompanying drawings, wherein like reference characters refer to similar parts throughout the several views and in which:

DESCRIPTION OF THE PREFERRED EMBODIMENTS OF THE INVENTION

Figure 1:
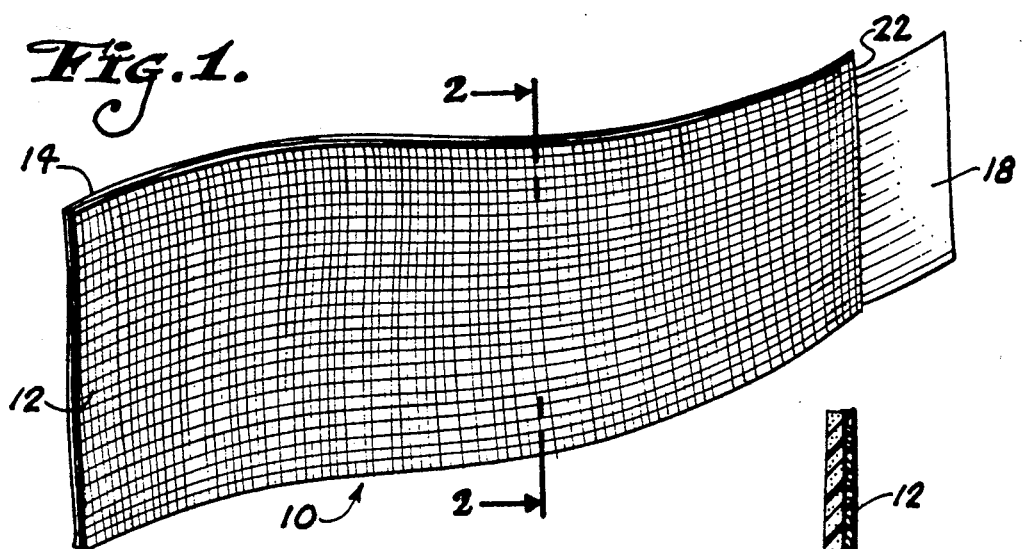
FIG. 1 is a top perspective view of the foam plastic orthopedic fabric of the present invention.
Figure 2:
FIG. 2 is an enlarged, cross-sectional view taken along line 2—2 on FIG. 1, looking in the direction of the arrows.
Figure 3:
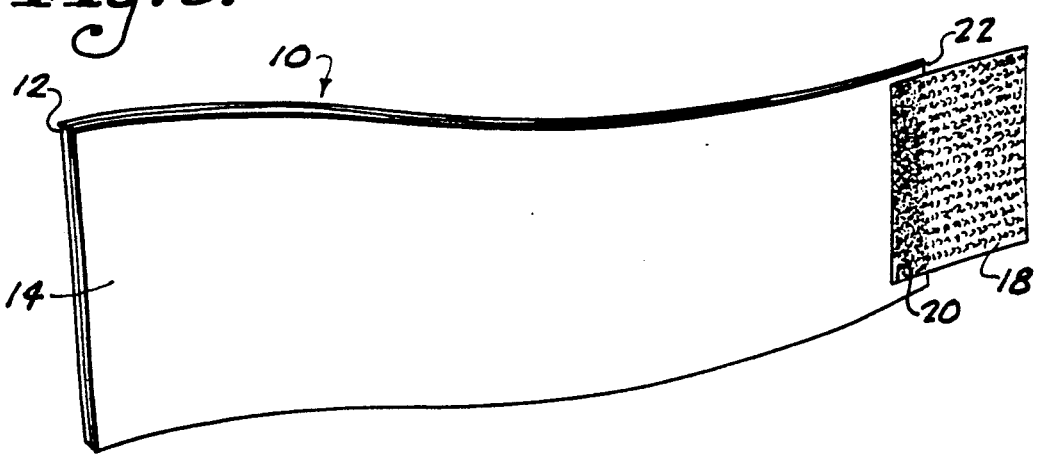
FIG. 3 is a bottom perspective view of the foam plastic orthopedic fabric of the present invention.

Although specific terms are used in the following description for the sake of clarity, these terms are intended to refer only to the particular structure of the invention selected for illustration in the drawings, and are not intended to define or limit the scope of the invention.

Referring now to the drawings, there is shown in FIG. 1 one embodiment of a foam plastic orthopedic fabric 10 constructed in accordance with the teachings of the present invention. The fabric 10 comprises generally an elongate length of unbroken loop fabric 12 which may be elasticized, having fastening properties, similar to that of "VELCRO" brand or similar material suitable for releasable connection to a cooperating strip of hook-type fastening material. The unbroken loop fabric 12, when utilized in a support device, can be either stretchable with elasticity both in the longitudinal direction and in the transverse direction or non-stretchable. When employed as an immobilizing device, the unbroken loop fabric 12 is preferably non-stretchable. When employed as a support device, the fabric 12 is preferably stretchable.

A second stretchable foam plastic layer 14 is intimately bonded to the unbroken loop fabric layer or sheet 12 without employing additional materials such as stitching, rivets, staples, etc. in an automatic, heat applied, bonding process. It is intended that the foam plastic layer 14 be formed of a foam of the urethane family having properties suitable to make it particularly useful as a bandage. Preferably, the foam plastic layer 14 is stretchable in both the longitudinal and transverse directions to make it completely compatible for use in combination with the unbroken loop fabric layer 12, whether of stretchable or non-elastic properties. The foam plastic layer 14 should be non-cydotoxic, breathable, of sufficient thickness to provide satisfactory cushioning over the portion 24 of the human body to be treated with the orthopedic fabric 10.

As best seen in FIG. 1, a tab 18 comprising a short length of "VELCRO" brand or similar non-elastic hook or fastener material is secured to the stretchable foam plastic layer 14 near one end 22 thereof without stitching, in known manner, for example, by employing heat sealing or other type of radio frequency or ultrasonic frequency junction 20 which is capable of producing sufficient thermal energy to at least partially melt the plastic foam causing it to partially liquify, thereby becoming a bonding agent. Alternately, the tab 18 could be adhesively or otherwise secured near one end of the unbroken loop fabric substrate 12 near one end thereof without employing additional materials.

Figure 4:
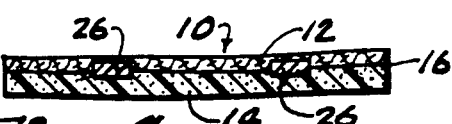
FIG. 4 is a cross sectional view similar to FIG. 2 and illustrating a modified embodiment of the invention.
Figure 5:
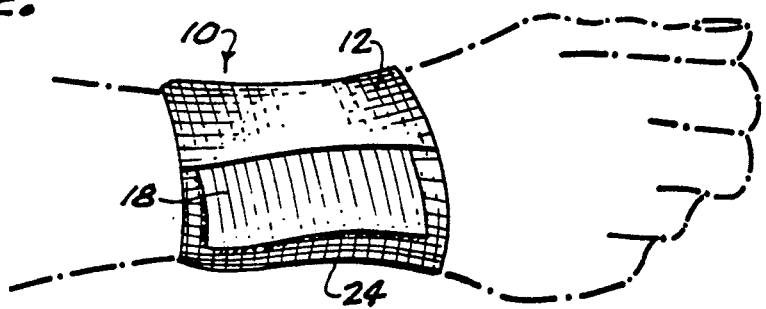
FIG. 5 is a perspective view showing the foam plastic orthopedic fabric in use about a portion of the human body to be treated.

If desired, as illustrated in FIG. 4, one or more strengthening stays 26 can be inserted intermediate the unbroken loop fabric layer 12 and the stretchable foam plastic layer 14 for strengthening purposes at the time the orthopedic fabric 10 is fabricated. Optionally, it is contemplated that an additional fabric and/or foam layer (not shown) could be applied over and secured to one of the bonded layers 12, 14 to secure one or more stays exteriorly to the bonded orthopedic fabric 10. Such stays 26 could find utility for bracing purposes, such as a back support or for additional bracing or strength when wrapped about a body member, such as a wrist 24 or perhaps an ankle (not illustrated) as may be indicated to meet individual requirements. The strengthening stays 26 may be permanently inserted at the interface 16 between the layers 12, 14 or may be temporarily inserted between the orthopedic fabric 10 and the additional fabric and/or foam layer above mentioned.

While the orthopedic fabric 10 has been illustrated in elongate, rectangular configuration, it will be appreciated that the orthopedic fabric 10 can be formed to any size sheet configuration and then cut to a preselected size and/or shape to cover a specific body portion in a manner capable of being wrapped thereabout. In other words, for example, the size and shape of orthopedic fabric 10 suitable to be wrapped around a wrist portion 24 will be of much smaller size and of different configuration than when the orthopedic fabric 10 is intended to be wrapped about other portions of the body (not shown) of a user, for example, to provide additional support for the user's back.

The invention further comprises the process of fabricating and using a stretchable or non-stretchable fabric substrate of unbroken loop fabric having fastening properties in combination with an intimately bonded thermoplastic foam substrate for use in orthopedic work. It is contemplated that the thermoplastic foam substrate 14 can be foamed directly upon the stretchable or non-stretchable unbroken loop fabric layer 12 in a manner suitable to assure overall bonding of the two materials in the preferred embodiment. Alternately, it is contemplated that the thermoplastic foam layer 14 can be suitably secured to the unbroken loop fabric 12 by adhesively bonding or by applying thermal energy such as by ultrasonic welding. Other methods of securing the two layers together that may alternately be employed in known manner can also comprise utilizing a transfer coating process, a cast on coating process, a flame laminating process or an adhesive bonding process.

By utilizing the orthopedic fabric 10 of the present invention, a universal product can be developed that is both lighter in weight and less expensive in fabrication inasmuch as automatic heat sealing is employed throughout without any requirement for hand stitching or other such manual operations. The fabric can be stretchable both longitudinally and laterally or can be non-stretchable and can be readily cut to any required size. The material is breathable, nontoxic and can provide a large degree of cushioning to the affected area. Further, the material is stretchable and completely adjustable to provide the required support. When additional support or strengthening may be required, semi-rigid stays may be secured between the fabric layers 12, 14 at the interface 16 thereof at the time of fabrication or the stays may be secured between the orthopedic fabric 10 and an additional layer as hereinbefore set forth.

In an important embodiment of the invention, the selective application of electrically deposited flock into the foam layer 14 at the time of foam curing can be made. The flock creates a soft surface in the foam layer 14 in a manner to enhance breathability and moisture and vapor transfer. The flock renders the foam layer surface so soft that it acts as a lubricant in a manner to prevent skin chafing.

Although the invention has been described with a certain degree of particularity, it is understood that the present disclosure has been made only by way of example and that numerous changes in the details of construction and the combination and arrangement of parts may be resorted to without the parting from the spirit and scope of the invention. Thus, the scope of the invention should not be limited by the foregoing specification, but rather, only by the scope of the claims appended hereto.

What is claimed is:

1. An orthopedic fabric comprising:
  a layer of unbroken loop fabric of preselected length defined between a first end and a second end, the fabric defining a receiving surface which is removably engageable with hooks of a hook and loop type closure;
  a layer of elastomeric foam comprising thermoplastic urethane of length similar to that of the fabric layer, the foam layer being in contact with and adhered to the fabric layer; and,
  hook means removably engageable with the layer of unbroken loop fabric and secured to the layer of unbroken loop fabric, the hook means being operable to releasably attach portions of said fabric together.

2. The orthopedic fabric of claim 1, wherein the foam layer is intimately bonded to the fabric layer in all areas of contact.

3. The orthopedic fabric of claim 1, wherein said hook means secured to the layer of unbroken loop fabric is permanently affixed by heat sealing.

4. The orthopedic fabric of claim 1, further comprising at least one stay secured in the orthopedic fabric intermediate the unbroken loop fabric layer and the foam layer.

5. The orthopedic fabric of claim 1, further comprising flock applied to the foam layer.

6. The orthopedic fabric of claim 1, further comprising a strengthening stay in contact with one of the fabric and the foam layer.

7. An orthopedic fabric comprising:
  a layer of unbroken loop fabric of preselected length defined between a first end and a second end, the fabric defining a receiving surface which is engageable with hooks of a hook and loop type closure;
  a layer of elastomeric foam comprising thermoplastic urethane of length similar to that of the fabric layer, the foam layer being intimately bonded to the fabric layer by diffusion of the thermoplastic urethane into the fabric layer; and,
  hook means engageable with the layer of unbroken loop fabric and secured to the layer of unbroken loop fabric, the hook means being operable to releasably attach portions of said fabric together.

8. The orthopedic fabric of claim 7, wherein the elastomeric foam is bonded to the unbroken loop fabric by collapsed liquified foam diffused into the unbroken loop fabric.

9. The orthopedic fabric of claim 7, wherein the hook means is attached to at least one of the foam and the fabric by collapsed liquified foam diffused into the hook means.

10. The method of fabricating an orthopedic fabric, comprising:
  forming a length of unbroken loop fabric, the fabric defining a receiving surface which is removably engageable with hooks of a hook and loop type closure;
  adhering a layer of thermoplastic elastomeric foam to the fabric, the thermoplastic foam being of a type which is a flowable liquid before curing and which collapses into a flowable liquid with application of heat energy;
  permanently securing a hook fastener to one of the unbroken loop fabric and the foam layer by engaging the flowable liquid with the hook fastener and allowing the same to harden;
  readily engaging and disengaging the hook fastener and the unbroken loop fabric.

11. The method of claim 10, wherein the adhering comprises curing the foam directly upon the unbroken loop fabric, the flowable liquid engaging with the unbroken loop fabric and becoming permanently attached during curing.

12. The method of claim 10, wherein the adhering comprises subjecting the foam layer to heat energy sufficient o melt surface portion of the foam layer and applying the melted surface portions directly to at least one of the unbroken loop fabric and the hook fastener.

13. The method of claim 17, wherein the subjecting comprises using radio frequency to produce the heat energy.

14. The method of claim 12, wherein the subjecting comprises using ultrasonic frequency to produce the heat energy.

15. The method of claim 10, further comprising the selective application of flock directly into the foam layer while uncured, the flock adhering in the thermoplastic foam.

16. The method of claim 15, wherein the application of flock is by electrostatic deposition.

17. The method of claim 10, further comprising applying at least one stay in contact with at least one of the unbroken loop fabric and the foam layer.

18. The method of fabricating an orthopedic fabric, comprising:

forming a length of unbroken loop fabric, the fabric defining a receiving surface which is removably engageable with hooks of a hook and loop type closure;

adhering a layer of thermoplastic elastomeric foam to the fabric, the thermoplastic foam being of a type which if a flowable liquid before curing and which collapses into a flowable liquid with application of heat energy;

forming at least one seam with a portion of the unbroken loop fabric by application of heat energy to collapse the foam into a flowable liquid which bridges the seam and thereafter hardens at a thickness less than the foam.

19. The method of claim 18, wherein the seam permanently secures a hook fastener to one of the unbroken loop fabric, whereby the hook fastener and the unbroken loop fabric are readily engageable and disengageable to form a closure with the unbroken loop fabric.

* * * * *